United States Patent
Hovde et al.

(10) Patent No.: US 9,110,006 B1
(45) Date of Patent: Aug. 18, 2015

(54) FREQUENCY-FEEDBACK CAVITY ENHANCED SPECTROMETER

(71) Applicant: Southwest Sciences Incorporated, Santa Fe, NM (US)

(72) Inventors: David Christian Hovde, Cincinnati, OH (US); Anthony Gomez, Santa Fe, NM (US)

(73) Assignee: Southwest Sciences Incorporated, Santa Fe, NM (US)

( * ) Notice: Subject to any disclaimer, the term of this patent is extended or adjusted under 35 U.S.C. 154(b) by 0 days.

(21) Appl. No.: 14/309,495

(22) Filed: Jun. 19, 2014

(51) Int. Cl.
   *G01J 3/10* (2006.01)
   *G01N 21/25* (2006.01)

(52) U.S. Cl.
   CPC .................................. *G01N 21/255* (2013.01)

(58) Field of Classification Search
   CPC ........................................................ G01J 3/10
   USPC ............................. 250/393, 343, 205, 227.11
   See application file for complete search history.

(56) References Cited

U.S. PATENT DOCUMENTS

| | | | |
|---|---|---|---|
| 5,903,358 A * | 5/1999 | Zare et al. ..................... | 356/437 |
| 6,882,432 B2 | 4/2005 | Deck | |
| 6,924,898 B2 | 8/2005 | Deck | |
| 7,301,639 B1 | 11/2007 | Kebabian et al. | |
| 7,805,980 B2 | 10/2010 | Kosterev | |
| 8,327,686 B2 | 12/2012 | Kachanov et al. | |
| 8,539,816 B2 | 9/2013 | Kachanov et al. | |
| 2003/0160148 A1* | 8/2003 | Yao et al. ..................... | 250/205 |
| 2011/0214479 A1 | 9/2011 | Kachanov et al. | |
| 2012/0212731 A1 | 8/2012 | Loock et al. | |
| 2013/0083328 A1 | 4/2013 | Koulikov et al. | |

FOREIGN PATENT DOCUMENTS

RU 2234779 8/2004

OTHER PUBLICATIONS

Busch, et al., "Cavity-ringdown spectroscopy: an ultratrace-absorption measurement technique", vol. 720, American Chemical Society, 1999, 133-134.

Engel, et al., "Innovations in Cavity Enhanced Laser Absorption Spectroscopy: Using in situ Measurements to Probe the Mechanisms Driving Climate Change", NASA Earth Science Technology Conference 2003, 2003.

Engeln, et al., "Phase shift cavity ring down absorption spectroscopy", Chemical Physics Letters, 1996, 105-109.

Hawe, et al., "CO2 monitoring and detection using an integrating sphere as a multiplass absorption cell", Measurement Science and Technology, 2007, 3187.

(Continued)

*Primary Examiner* — David Porta
*Assistant Examiner* — Faye Boosalis
(74) *Attorney, Agent, or Firm* — Jeffrey D. Myers; Peacock Myers, P.C.

(57) ABSTRACT

A spectrometer comprising an optical cavity, a light source capable of producing light at one or more wavelengths transmitted by the cavity and with the light directed at the cavity, a detector and optics positioned to collect light transmitted by the cavity, feedback electronics causing oscillation of amplitude of the optical signal on the detector at a frequency that depends on cavity losses, and a sensor measuring the oscillation frequency to determine the cavity losses.

20 Claims, 6 Drawing Sheets

(56) References Cited

OTHER PUBLICATIONS

Herbelin, et al., "Sensitive measurement of photon lifetime and true reflectances in an optical cavity by a phase-shift method", Applied Optics, 1980, 144-147.

Kebabian, et al., "Detection of nitrogen dioxide by cavity attenduated phase shift spectroscopy", Analytical Chemistry, 2003, 724-729.

Masiyano, et al., "Gas cells for tunable diode laser absorption spectroscopy employing optical diffusers: Part 2: Intergrating spheres", Applied Physics B, 2010, 303-312.

Medhi, "Intracavity Laser Absorption Spectroscopy Using Quantum Cascade Laser and Fabry-Perot Interferometer", Dissertation, Department of Physics, College of Sciences, University of Central Florida, 2011.

Paldus, et al., "An historical overview of cavity-enhanced methods", Can. J. Phys., 2005, 975-999.

Paldus, et al., "Cavity-locked ring-down spectroscopy", Journal of Applied Physics, 1998, 3991-3997.

Pipino, et al., "Evanescent wave cavity ring-down spectroscopy with a total-internal-reflection minicavity", Review of Scientific Instruments, 1997, 2978-2989.

Romanini, et al., "Introduction to Cavity Enhanced Absorption Spectroscopy", Chapter 1, Cavity-Enhanced Spectroscopy and Sensing, G. Gagliardi-P. Loock, eds., 2014.

Romanini, et al., "Optical-feedback cavity-enhanced absorption: a compact spectrometer for real-time measurement of atmospheric methane", Applied Physics B, 2006, 659-667.

Tarsa, et al., "Single Cell detection by cavity ring-down spectroscopy", Appl. Phys. Lett., 2004, 4523-4525.

Ye, et al., "Cavity-Enhanced Frquency Modulation Spectroscopy: Advancing Optical Detection Sensitivity and Laser Frequency Stabilization", SPIE—Methods for Ultrasensitive Detection, 1998, 85.

Ye, et al., "Using FM Methods with Molecules in a High Finesse Cavity: A Dmonstrated Path to < 10-12 Absorption Sensitivity", ACS Symposium Series, vol. 720, American Chemical Society, 1999, 233-256.

\* cited by examiner

FREQUENCY-FEEDBACK CAVITY ENHANCED SPECTROMETER

STATEMENT REGARDING FEDERALLY SPONSORED RESEARCH OR DEVELOPMENT

This invention was made with government support under Contract No. DE-SC0007534 awarded by the U.S. Department of Energy. The government has certain rights in the invention.

CROSS-REFERENCE TO RELATED APPLICATIONS

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field)

The present invention relates to absorption spectroscopy, particularly to cavity-enhanced absorption spectroscopy.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

The field of cavity-enhanced spectroscopy has been the focus of intense activity as a result of the high sensitivity that can be obtained from a compact and relatively simple apparatus. The apparatus includes a light source, a detector, and an optical cavity that contains the sample to be measured (typically a gas or liquid, but sometimes an optical component), together with some means of quantifying the light transmitted through the cavity.

Cavity enhancement refers to the increase in absorption signal (relative to a single pass measurement) when light passes through an optical cavity of two or more mirrors, typically formed by depositing dielectric coatings on their surfaces to achieve power reflectivity >99%. Resonant light from inside the cavity leaks out through the mirrors with a characteristic time scale known as the cavity lifetime. The spacing of the mirrors depends on the application but is typically in the range from about one millimeter to about one meter. By measuring a cavity-enhanced signal, a spectrum of the sample can be recorded, or the optical losses due to the sample can be estimated. These losses can be used to quantify the amount of sample in the cavity, for instance the concentration of methane in a sample of room air. High sensitivity to small optical losses is obtained in part because light that enters the cavity makes a large number of passes through the cavity before it leaks out through one on the mirrors to a detector. There are a large number of variations on the method. The field has been reviewed, e.g., in Gagliardi, G., et al., Cavity-Enhanced Spectroscopy and Sensing, Springer Series in Optical Sciences (Book 179) (2014), Paldus, B. A., et al., "An historical overview of cavity-enhanced methods", Canadian Journal of Physics 83(10), 975-999 (2005), and Busch, K. W., et al., Cavity-ringdown spectroscopy: an ultratrace-absorption measurement technique (Vol. 720), American Chemical Society (1999).

A variety of detection methods can be used with continuous wave (CW) light sources. The simplest approach—"integrated cavity output spectroscopy"—measures the average optical power transmitted through the cavity. This approach has the advantage of simple implementation, but the disadvantage that the signal depends not just on losses in the cavity, but also on losses in the optical path outside the cavity and on variations in the efficiency of both the source and the detector.

In the "Ring-down" approach, the amplitude of the light source is modulated rapidly compared to the cavity lifetime, for instance using an acousto-optical modulator to deflect a laser, or by modulating the current injected into a semiconductor device such as a light emitting diode. Light shines on the cavity and after it has built up to a sufficient level, the beam is shut off and the decay of light from the cavity is recorded—the "cavity ring-down." This approach has the advantage that the shape of the decay curve can be analyzed. In the simplest case, the shape is a single exponential decay, which is characterized by a single time constant, $\tau$. A variety of effects can lead to multi-exponential decay, which may require a more sophisticated analysis to determine precisely the cavity losses. A disadvantage of the ring-down approach is that the recording rate has to be significantly faster than the cavity lifetime. This high recording rate becomes especially problematic when the cavity lifetime is short.

Phase Shift Cavity Enhanced Absorption Spectroscopy or Cavity Attenuated Phase Shift Spectroscopy, Herbelin, J. M. et al., "Sensitive measurement of photon lifetime and true reflectances in an optical cavity by a phase-shift method", Applied Optics, 19(1), 144-147 (1980); Engel, G. S., et al., "Innovations in cavity enhanced laser absorption spectroscopy: Using in situ measurements to probe the mechanisms driving climate change", In Earth Science Technology Conference, Laser Sensor Technologies (2003); Kebabian, P. L., et al., "Detection of nitrogen dioxide by cavity attenuated phase shift spectroscopy", Analytical Chemistry 77(2), 724-728 (2005), measures losses in a cavity by measuring the phase shift of the modulation frequency of modulated light transmitted through the cavity. The amplitude of the light incident on the cavity is modulated. A fixed modulation frequency f is usually chosen to be close to $2\pi/\tau$ to optimize sensitivity to changes in $\tau$. Because the amplitude of the light incident on the cavity is modulated, the amplitude of the light transmitted through the cavity is also modulated, but the amplitude of the modulation and its phase change as a result of the time spent on average in the cavity. When the cavity exhibits simple exponential decay, the phase, $\theta$, of the transmitted light is shifted by:

$$\tan(\theta) = -2\pi f\tau.$$

Thus, a measurement of the cavity phase shift $\theta$ is equivalent to a measurement of ring down time T, and both can be related to the losses in the cavity and hence of the concentration of analytes in the cavity. U.S. Patent Publication No. 20120212731 to Loock extends this approach by describing a method for measuring the phase shift of a cavity at several modulation frequencies in order to account for multi-exponential decay waveforms in the cavity. This method also allows the use of two light sources, each modulated at its own frequency, for detecting simultaneously in more than one wavelength band. The modulation frequencies are chosen ahead of time such that they and their harmonics don't interfere. Once these modulation frequencies have been chosen, Loock measures the phase of the transmitted signal. All these phase shift cavity enhanced methods require the accurate measurement of a phase. Furthermore, all these methods require the choice of a modulation frequency that optimizes the sensitivity of the spectrometer. The sensitivity may degrade if large concentrations of an analyte are present, which would cause a significant change in $\tau$ such that the modulation frequency f was no longer about equal to $2\pi/\tau$. The calibration of the spectrometer depends on the calibration of the phase shift measurement. If the phase shift measurement is implemented by separate analog x and y demodulations, then gain errors between the x and y channels can introduce calibration errors. If the phase measurement is implemented by digital means, then digitization effects may limit the resolution with which the phase can be measured. For instance, the SR830 digital lock-in amplifier from Stanford Research has a phase resolution of 0.01 degrees. This is equivalent to a noise level of about 0.00017 of the detected light. This is one hundred times greater than the shot noise of a 100 nW optical signal in a 1 Hz bandwidth. Thus, detection with such a lock-in amplifier will not achieve the full theoretical precision. Furthermore, digital phase detection methods are difficult to apply at high frequencies associated with cavities that have short storage times.

The "NICE-OHMS" method is presented in Ye, J., et al., "Cavity-enhanced frequency modulation spectroscopy: advancing optical detection sensitivity and laser frequency stabilization", Optoelectronics and High-Power Lasers & Applications (pp. 85-96), International Society for Optics and Photonics (1998) and Ye, J., et al., "Using FM Methods with Molecules in a High Finesse Cavity: A Demonstrated Path to <10-12 Absorption Sensitivity", in ACS Symposium Series (Vol. 720, pp. 233-256), American Chemical Society (1999). The authors use modulation of the wavelength of the light source at a frequency that exactly matches the free spectral range of the cavity. The modulation frequency is therefore fixed. Power builds up in the cavity at the laser wavelength and at the sidebands that match cavity resonances. Under this condition, the amplitude of the light transmitted through the empty cavity is not modulated. When a wavelength-dependent absorption feature is present, it interacts more strongly with one of the sidebands, and this unbalances the transmitted power so that the light transmitted by the cavity is modulated. The information about the concentration of the absorbing species is carried by the amplitude of the modulation.

Many researchers have used modulation techniques to lock the wavelength or frequency of a laser to a particular cavity resonance. Typically, the wavelength of the light source is modulated by a small amount compared to the cavity width, and the light transmitted or reflected by the cavity is measured by lock-in demodulation. The wavelength of the laser or the length of the cavity is adjusted so that the cavity mode and the laser maintain an alignment in wavelength. In the work of Romanini, D., et al. "Optical—feedback cavity—enhanced absorption: a compact spectrometer for real-time measurement of atmospheric methane." Applied Physics B 83.4, 659-667 (2006), optical feedback from the cavity to a laser caused the laser to lock to a particular cavity mode by adjusting the laser frequency. In neither of these cases is the information about cavity losses encoded as a variable modulation frequency.

A number of researchers have used information about the phase and amplitude of spectroscopic signals to improve the spectrometer. U.S. Pat. No. 7,805,980 to Kosterev describes a photoacoustic gas analysis spectrometer in which a relatively high modulation frequency for the light source is chosen so that the time lag associated with conversion of the absorbed optical energy into an acoustic wave results in significant phase shift. The information about the concentration of the analyte is contained in the amplitude of the acoustic signal, while the phase of the signal at some pre-determined frequency confirms the identity of the analyte. When two analytes absorb light of the same wavelength, it is still possible to distinguish the concentrations of the two by choosing a detection phase that is orthogonal to the interfering analyte. U.S. Patent Publication No. 20110214479 to Kachanov discloses a photoacoustic gas detection apparatus that includes lock-in detection by multiplying a signal by a sine and cosine reference function that have a constant phase relative to a modulation function. The frequency of the modulation function is chosen to match the resonant condition that enhances the signal from the acoustic cavity-microphone system. The concentration information is derived from the amplitude of the detected signal. All these photoacoustic approaches require the measurement of the amplitude of a signal from a microphone to determine the concentration of a species in the spectrometer.

Other arguably related references in the field include U.S. Patent Publication No. 20130083328 to Koulikov, U.S. Pat. No. 6,924,898 to Deck, and U.S. Pat. No. 7,301,639 to Kebabian.

BRIEF SUMMARY OF THE INVENTION

The present invention is of a spectrometer (and concomitant methods) comprising: an optical cavity; a light source capable of producing light at one or more wavelengths transmitted by the cavity and with the light directed at the cavity; a detector and optics positioned to collect light transmitted by the cavity; feedback electronics causing oscillation of amplitude of the optical signal on the detector at a frequency that depends on cavity losses; and a sensor measuring the oscillation frequency to determine the cavity losses. In the preferred embodiment, the light source is an LED, SLED, laser, or a lamp. Amplitude of the light source may be modulated. Wavelength or frequency of the light source is modulated so as to modulate the light transmitted by the cavity. The cavity comprises at least two mirrors enclosing a gaseous or liquid sample. The cavity comprises at least two mirrors enclosing a suspension. The cavity comprises one or more surfaces that use total internal reflection arranged so that an evanescent field is in contact with a sample. The cavity comprises an optical fiber made so that an evanescent field of the optical fiber can interact with a sample. The cavity can comprise an integrating sphere. One or more amplifiers and/or phase shifters are arranged to create self-oscillation at a target frequency. A phase locked loop is employed, preferably generating a clock signal that is an integer ratio of the oscillation frequency, wherein the clock signal is used to generate a phase-shifted modulation frequency, and wherein the clock signal produces a number of preset phases. Most preferably the preset phases are chosen to keep the oscillation frequency within a target range of frequencies, wherein the oscillation frequency is measured at a number of preset modulation phases and the resulting frequencies are combined to determine an estimate of cavity loss that is substantially independent of multiexponential behavior of the cavity.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention can measure the losses in an optical cavity without requiring a careful measurement of the amplitude of the detection signal. The invention does not require careful adjustment of the relative gains of two amplifiers. The invention does not require a microphone or an acoustic resonance frequency. The invention does not require a linear, calibrated phase detector. The invention operates at the most sensitive frequency regardless of changes in the optical losses within the cavity.

For purposes of the specification and claims, the following definitions are employed: Light means electromagnetic radiation regardless of wavelength or energy. Modulation means a method for changing the amplitude, phase, or frequency of light. Detector means a device that can produce an electrical signal proportional to the power or intensity or electric field of the light that is incident on the detector. Optical path means the distance a photon travels through the sample before reaching the detector. Average optical path means the average of the optical paths of an ensemble of photons. An Optical Cavity here means mirrors, windows and/or other optical elements that cause light to be reflected or scattered a number of times, such that the optical path is substantially longer than a direct path through the sample and such that the optical paths comprise a range of values. Cavity Loss means any process inside the cavity that prevents optical power from reaching the detector. These processes could include optical absorption or optical scattering. An Empty Cavity is one in which the concentration of the analyte is zero. Gas or liquid (the sample matrix) may still be present in the cavity. Feedback means an electrical circuit that receives the signal from the detector and modifies it to generate a signal that is used to modulate the light.

Figure 1:
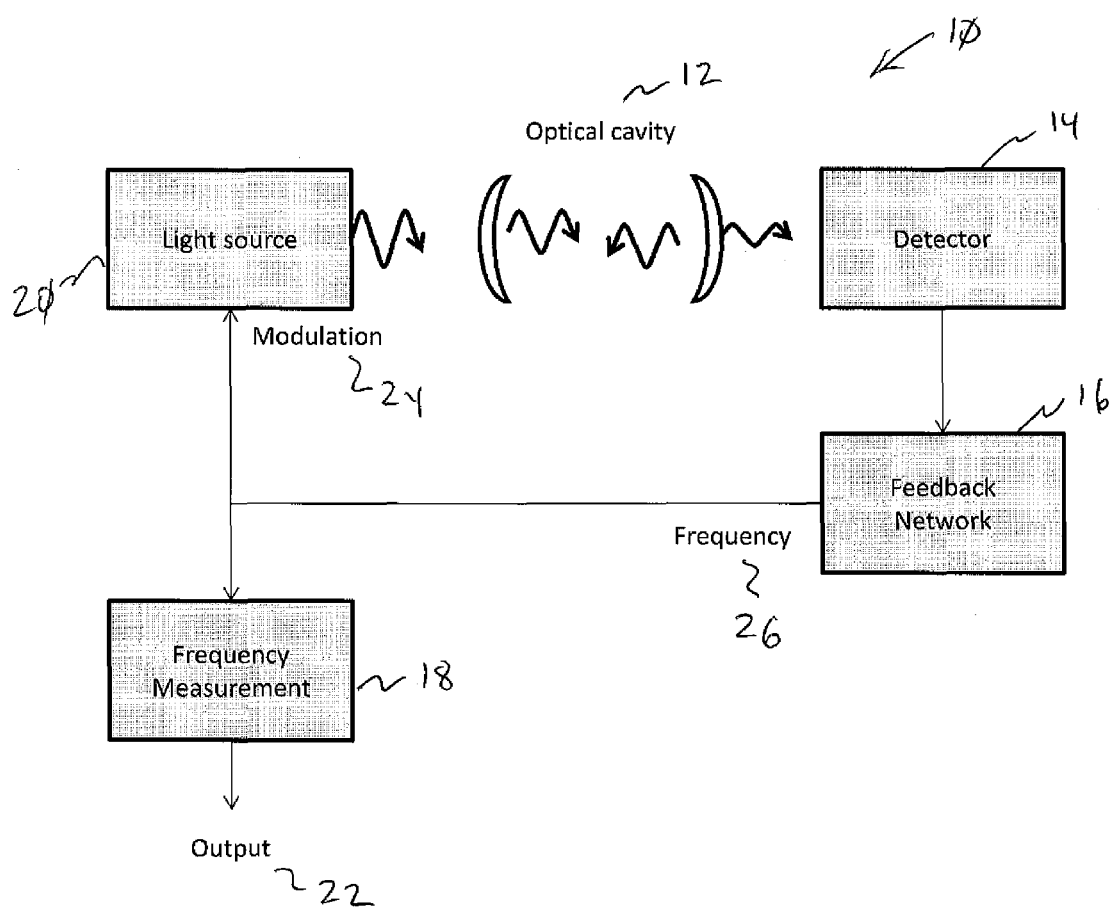
FIG. 1 shows basic elements of the frequency-feedback cavity enhanced spectrometer 10 of the invention. A detector 14 and electronics amplify the signal from the light transmitted through the cavity. A feedback network 16 changes the modulation frequency 26 as a function of cavity losses, such that the round-trip phase change remains constant. A light source 20 whose amplitude or wavelength can be modulated 24, such that the light transmitted through the cavity 12 is periodically modulated. The cavity's optical losses are to be measured 18, either to infer the contents of the cavity or to determine the quality factor of the cavity, providing output 22.

The invention comprises elements as shown in FIG. 1. These include a light source which can be modulated so that the power transmitted through the cavity is modulated, an optical cavity that receives light from the source, a detector and appropriate amplifier that generates a signal proportional to the optical power transmitted through the cavity, electronics to feed back the detected signal to modulate the light source at a frequency dependent on cavity losses, and electronics to measure the modulation frequency or period and thereby determine cavity losses.

Figure 2:
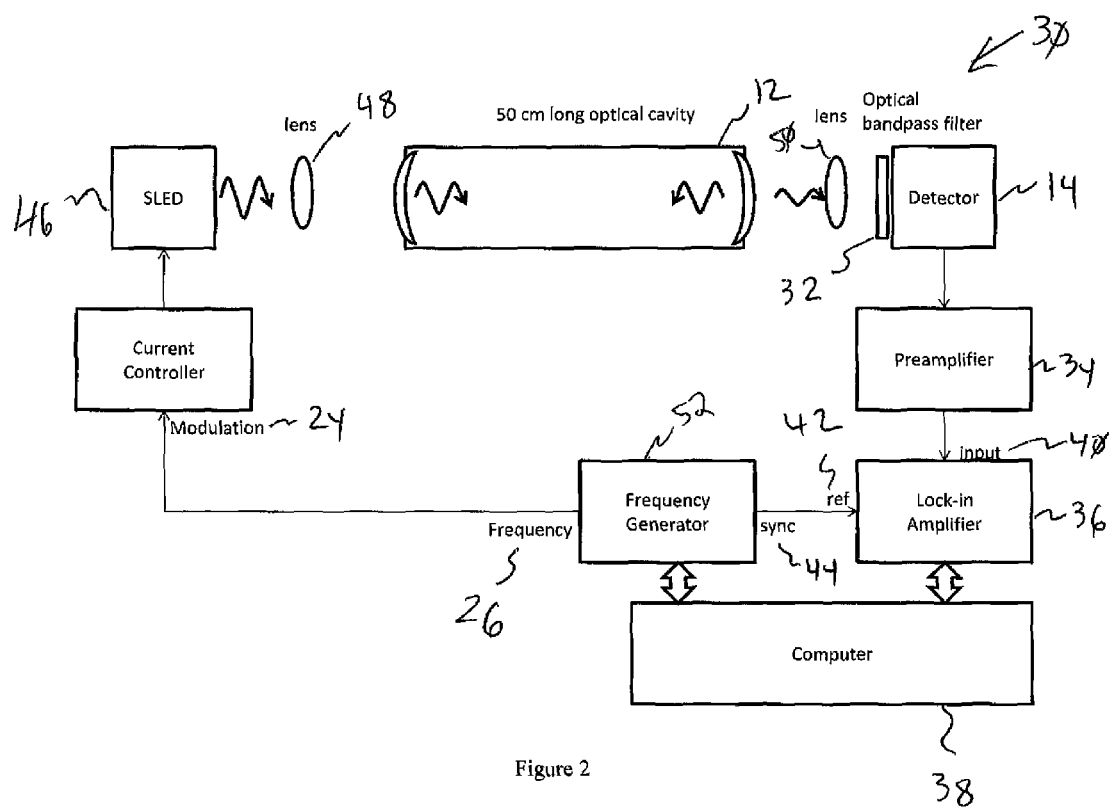
FIG. 2 shows an implementation of the frequency-feedback cavity enhanced spectrometer 30 of the invention, using a superluminescent diode 46 (SLED) operated by a current controller 24 and whose injection current can be modulated, a 50 cm long optical cavity 12, lenses 48,50 to couple the light into the cavity and to focus the transmitted light onto a detector 14, and optical filter 32 to restrict the spectral band of light detected, a pre-amplifier 34, a lock-in amplifier 36 referenced 42 to a synchronization 44 signal from frequency generator 52 and receiving input 40, and a computer 38 that reads the lock-in amplifier and writes the modulation frequency to the frequency generator. A feedback loop in the computer can be used to adjust the modulation frequency so as to drive the lock-in output to zero. The computer tracks the modulation frequency 26 required to achieve this condition. Changes in cavity losses due to the introduction of acetylene, for example, into the cavity result in changes in the operating frequency.

The invention is demonstrated herein with both a gas phase and a liquid phase sample, using broad band light sources (whose spectral output spans a large number of cavity modes) and a digital feedback loop. The gas phase demonstration used an incoherent, broad-band light source (a fiberized super-luminescent diode (SLED) with spectral wavelength of 1.55 μm and spectral bandwidth=60 nm) with the output of the fiber directed to an aspheric lens for cavity mode-matching (FIG. 2). The light source was modulated by applying a square wave from a computer controlled function generator (SRS DS345 was selected) to a current driver, resulting in 180 mA modulation and close to 100% modulation of the output of the SLED. An optical cavity was formed using two 99.995% reflective mirrors ($\lambda=1.54$ μm, bandwidth=120 nm, radius of curvature of about 2 m) spaced 50 cm apart. The theoretical ringdown time for this system is 33 μs, and the measured ringdown time was 37 μs. The average optical path is thus about 11 km, which far exceeds the physical path of 0.5 m. The transmitted optical power was detected by an InGaAs photodiode, amplified using a current preamplifier with suitable noise and bandwidth specifications (SRS SR570 was selected). The detector noise was within a factor of ten of the calculated shot noise for the detected photocurrent. A computer-controlled dual phase lock-in amplifier (SRS SR830 was selected) served as the phase detector. The lock-in has an arbitrary phase setting that can be chosen so that at a given frequency, the demodulated signal is almost all in the X or in-phase output of the lock-in. The lock-in can also provide the phase of the input relative to the arbitrary phase. A laptop was programmed to read the outputs of the lock-in and adjust the frequency of the function generator.

The laptop computer was used to close the feedback loop by updating the frequency of the function generator after measuring the phase or the out-of-phase signal transmitted through the cavity. The system was first set up with the feedback loop disabled. The lock-in phase was set to about 45° relative to the value obtained by bypassing the optical cavity, and the modulation frequency was adjusted to about 5 kHz. The detected signal appears mostly in the x output of the lock-in, as a result of the −45° phase shift of the cavity. Small adjustments to the modulation frequency could then drive the y output to zero. Using the output expand mode on the y output reduced bit noise in the phase measurement to an inconsequential level. Then the feedback loop was closed, using a proportional-integral loop running at a few Hz. The loop measured the y output of the lock-in and adjusted the modulation frequency to keep the y output near zero. Some experimentation was used to determine the proportional and integral gain needed to get stable performance. Once these constants were determined, the computer logged the oscillation frequency as a function of time.

Figure 4:
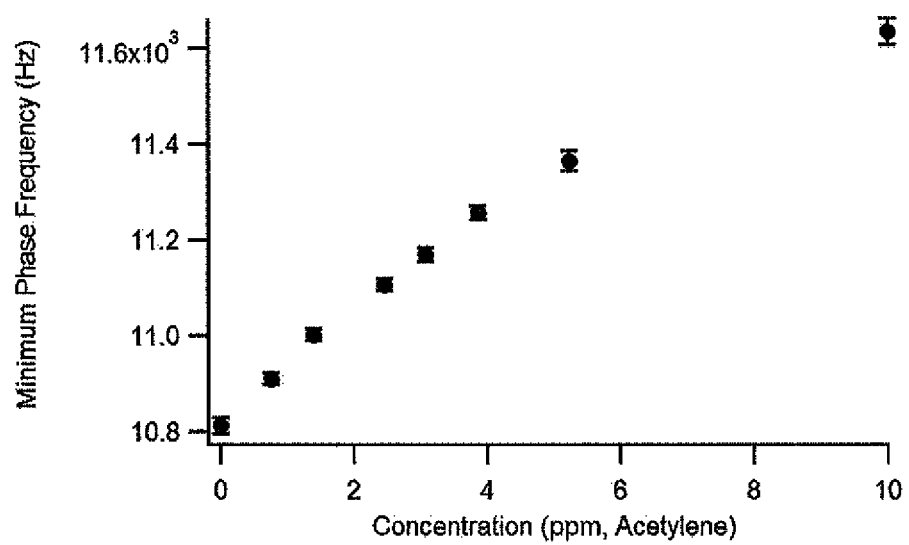
FIG. 4 shows measured oscillation frequencies vs. concentration of gaseous acetylene in the cavity of FIG. 2 at constant total pressure.
Figure 5:
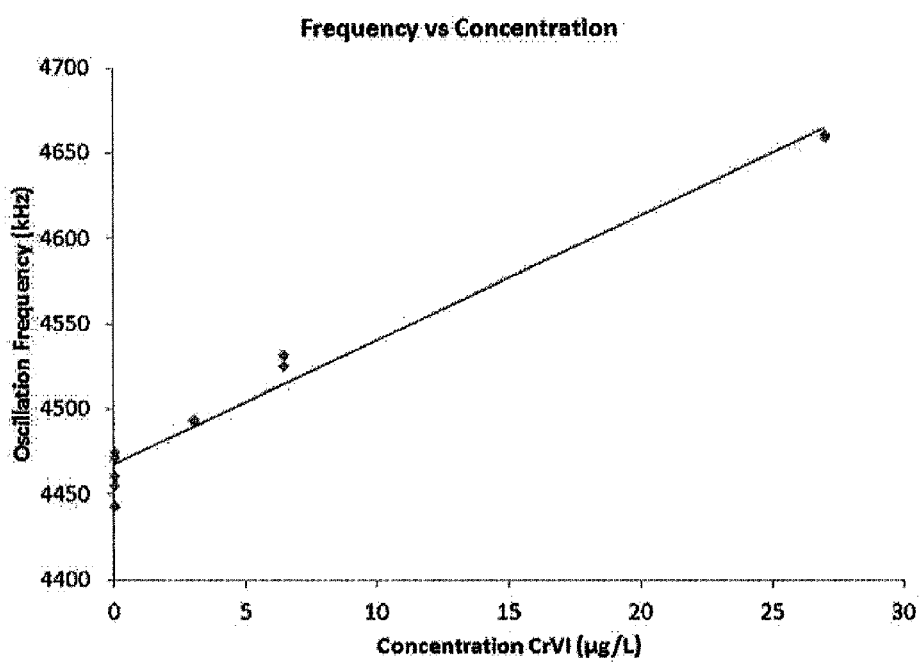
FIG. 5 shows measured oscillation frequency of the cavity of FIG. 3 vs. concentration of hexavalent chromium (CrVI) and the least-squares fit to the data.

Gaseous acetylene absorbs light in the wavelength range spanned by the light source and resonated by the cavity. When acetylene was added to the cavity, the modulation frequency increased, as expected due to the increased cavity loss. When the acetylene was removed from the cell, either by pumping out or by sweeping out with a flow of clean nitrogen, the modulation frequency returned to its starting value. A plot of modulation frequency vs acetylene concentration is shown in FIG. 4.

Figure 3:
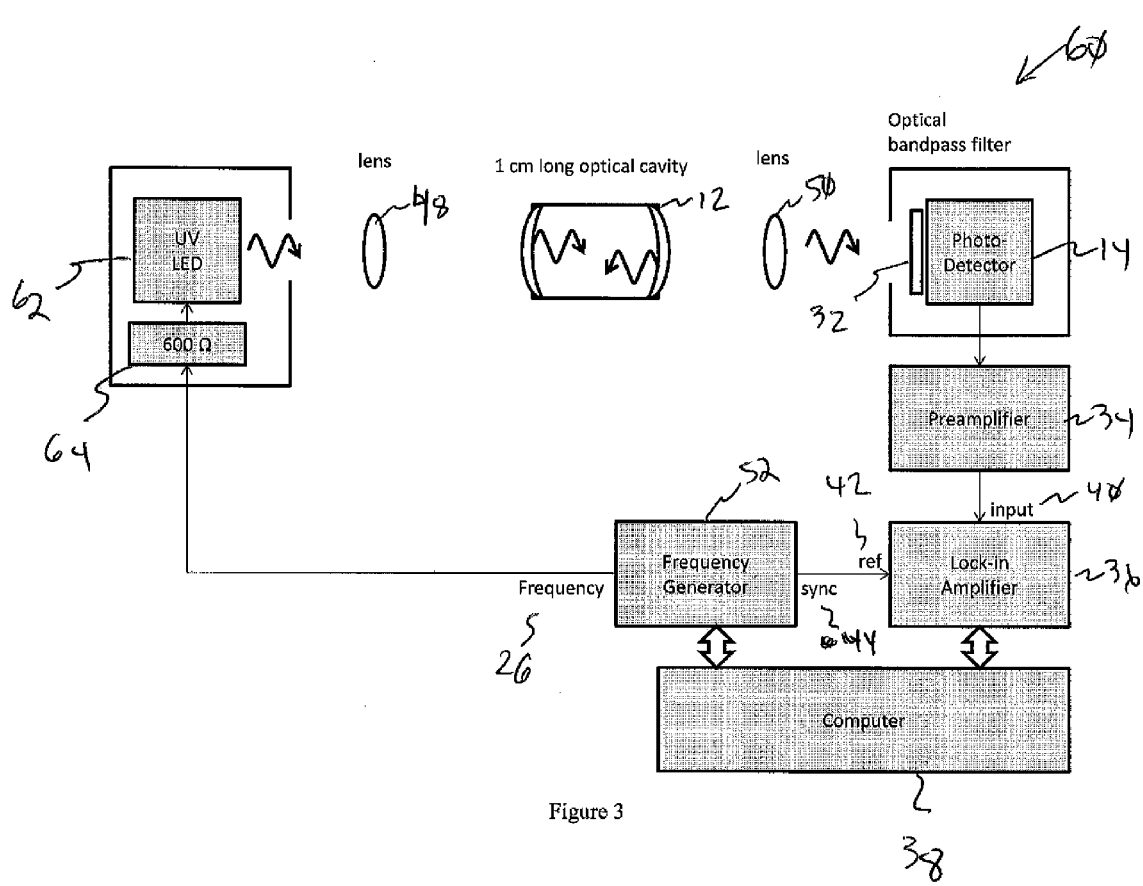
FIG. 3 shows an implementation of frequency-feedback cavity enhanced spectrometer 60 of the invention to measure, for example, a liquid sample using a UV LED as the light source. The LED 62 is operated directly from a frequency generator 52, using a resistor 64 to limit the current to its desired value. The frequency generator also has a dc offset that is used to set the quiescent point to its desired value. Lenses 48,50 focus the light into the cavity 12 and then onto a detector 14. The cavity is preferably water tight and provided with inlet and outlet ports so that it can be filled with a liquid sample. Both the detector and the LED are mounted inside shielded enclosures to reduce pick-up of the modulation signal onto the detection circuit. The lock-in amplifier 36, frequency generator and computer 38 are used in a similar fashion to those in FIG. 2.

A second demonstration was made using a liquid sample (hexavalent chromium in water) in a much smaller cavity (FIG. 3). The light source was an ultraviolet LED (Sensor Electronic Technology Inc, UVTOP model, 1.0 mW, nominal wavelength of 355 nm and spectral bandwidth of 14 nm) that includes a lens in the package that produces a focused spot about 5-10 mm from the tip of the LED. The beam was allowed to diverge after the focus, then re-imaged about 15 cm away at the cavity. The cavity consisted of curved mirrors that were dielectrically coated to achieve about 99.8% reflectivity in the range from 340 nm to 390 nm. Two of these mirrors were mounted on either end of an aluminum lens tube which included a side hole which could be used to introduce liquid samples using a plastic tube and syringe. The cavity spacing was varied between 3 and 30 mm, with a value of about 10 mm selected to give a balance between optical throughput (highest at small spacings) and useful oscillation frequency (also highest at small spacings).

Light coming out of the back mirror of the cavity was imaged onto a photodiode through an optical bandpass filter centered at 365 nm with a 25 nm pass band (Semrock Hg01-365-25). The optical filter was found to be essential: a small fraction of the light emitted by the LED is outside the bandwidth of the cavity mirrors. If it can reach the detector it produces a modulated background signal that does not depend on cavity loss. Also preferred for successful operation is minimizing electrical pick-up. The light passing to the detector only amounts to a few nW, giving rise to photocurrents of about ½ nA. The current that modulated the LED was about 20 mA, so coupling even a small fraction of this current into the detection circuit would cause a large spurious signal. To avoid pick-up, the LED and the detector/preamplifier were placed in separate shielded boxes, and the modulation current return was isolated from the detector circuit. The LED was driven directly from the function generator, using the offset of the function generator and a 6009Ω resistor to limit the current to an acceptable value and produce a modulation index near 100%. The amplified detector current was routed to a lock-in amplifier capable of measuring MHz signals (SRS 844 was used).

Samples of hexavalent chromium in water were prepared by dilution from commercial 10 ppm standards (Hoch) using filtered, deionized water. Prior to entering the cavity, the liquid samples passed through a 450 nm particle filter. Care was taken to avoid introducing bubbles into the cavity. The results are shown in FIG. 4 as points, together with a line representing a least squares fit to all the data. The slope of the line is 7.28 kHz/(μg/L). Five of the points were recorded at zero concentration. These points have a standard deviation of 12.8 kHz. Using the measured slope, this corresponds to noise in the range of measured concentrations of about 12.8/7.28=1.75 μg/L. Consistent with this estimate of the instrument resolution, step changes of 3 μg/L are clearly resolved over short time scales.

Figure 6:
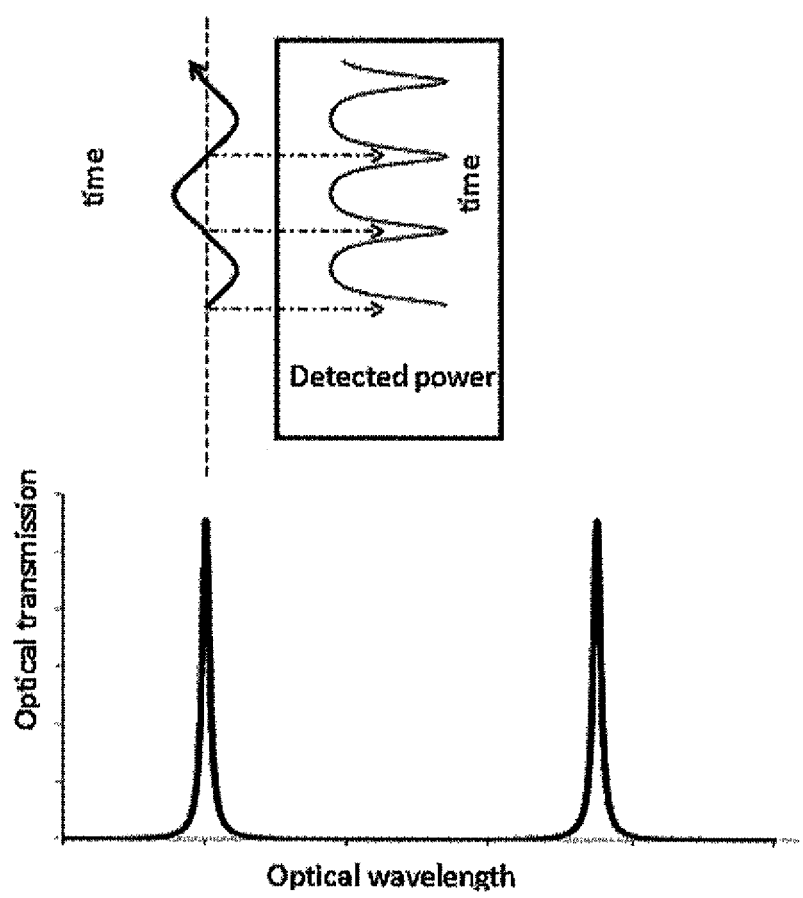
FIG. 6 shows in the bottom trace a calculated transmission spectrum of a cavity as the laser wavelength is slowly scanned through two transmission resonances. The upper arrow shows the laser wavelength as a function of time being modulated slowly across one of the resonances. The inset shows the detected power as a function of time. Modulation of the wavelength of a laser gives rise to modulation of the power transmitted through a cavity. When the center wavelength of the laser matches a cavity transmission resonance, the detected power oscillates primarily at twice the modulation frequency of the laser, increasing as the laser is tuned through the resonance. As the modulation frequency is increased, the peak-to-peak amplitude of the detected power will decrease and the phase will shift relative to the modulation waveform.

The light sources described above, a superluminescent light-emitting diode and a standard light emitting diode, are spectrally broad compared to the cavity free spectral range, so the light excites many cavity modes. It is possible to use a lamp as a broadband source. It is also possible to use this approach with a light source that excites just one or a few modes of the cavity. In this case, either the modulation should not interfere with locking the source wavelength to a cavity transmission wavelength (amplitude modulation could be accomplished, for instance, by using an acousto-optical modulator while accounting for its small frequency shift), or the wavelength of the source can be modulated in a way that creates the desired intensity modulation of the transmitted light, for instance by modulating the injection current of a tunable diode laser. FIG. 6 shows such a modulation scheme. When the laser wavelength is made to vary in time around a transmission resonance of the cavity, the detected optical power will also vary, but at twice the modulation frequency. Appropriate variations to the feedback circuit allow stable operation in this manner.

The SLED and UV-LED both emit a fixed band of wavelengths. For many applications, it will be better to provide a spectrally tunable light source, such as a tunable diode laser. The measured spectrum will consist of modulation frequency as a function of source wavelength. Such a spectrum can be analyzed to determine the concentration and identity of analytes in the cavity.

Cavity-enhanced spectroscopy can be performed with other configurations, such as with more than two mirrors, Paldus, B. A., et al., "Cavity-locked ring-down spectroscopy", Journal of Applied Physics, 83(8), 3991-3997 (1998), with a cavity in which the evanescent field is in contact with the sample (using total internal reflection as in Pipino, A. C., et al., "Evanescent wave cavity ring-down spectroscopy with a total-internal-reflection minicavity", Review of scientific instruments, 68(8), 2978-2989 (1997), or using an appropriate optical fiber as in Tarsa, P. B., et al., "Single cell detection by cavity ring-down spectroscopy", Appl. Phys. Lett. 85, 4523-4525 (2004)), with a cavity with off-axis excitation, a fiber cavity, or even with an integrating sphere. Hawe, E., et al., "CO2 monitoring and detection using an integrating sphere as a multipass absorption cell", Measurement Science and Technology, 18(10), 3187 (2007) and Masiyano, D., et al., "Gas cells for tunable diode laser absorption spectroscopy employing optical diffusers; Part 2: Integrating spheres". Applied Physics B, 100(2), 303-312 (2010). The methods described here could be used to measure cavity losses with all those cavity configurations.

The examples above involved detection of chemical compounds in the gas phase or in solution. This approach could also be used to characterize losses by the optics themselves. This approach could also be used to characterize scattering by a sample inside the cavity, for instance to determine the properties of a suspension or as a smoke detector.

The electronics used to demonstrate this technique, lock-in amplifiers and frequency generators, are available in many laboratories, but they are not especially compact or inexpensive. It is anticipated that many improvements could be made on the detection electronics to make them smaller and less expensive.

One approach is to use an amplifier together with fixed phase shifters to create a self-oscillating circuit. The circuit will have positive feedback at the oscillation frequency. This is achieved when the amplified signal undergoes gain and an overall −360° phase shift around the loop, so that initial small fluctuations at the oscillation frequency will build up to macroscopic signal. The cavity will give rise to a phase shift that depends on cavity losses. Assume that this phase shift for the empty cavity is chosen to be −45°. An additional −45° can be obtained with an RC low pass filter with a 3 dB point near $f=1/2\pi\tau$ for the empty cavity and a −90° phase shift can be obtained with an integrator. An inverting amplifier can supply the final −180° phase shift needed to reach a round trip phase shift of −360°. The design of these additional phase shifts sets the operating phase shift of the empty cavity. This approach needs enough net gain to build up to a macroscopic oscillation (including losses from the low pass filter), but it may require level limiting circuitry to avoid applying too large a modulation signal to the light source. In the case of many commercial diode laser controllers, such circuitry is already built-in. An advantage of this approach is that it does not require a phase comparator inside the loop.

Another approach is to use a phase-locked loop inside the feedback loop. A local oscillator is phase-locked to the signal from the detector, and the local oscillator is used to derive the modulation signal. In general there is a static phase shift between the detector signal and the locked oscillator that depends on the type of phase comparator used in the phase-locked loop. There will be an additional phase shift that is required to provide the required −360° phase shift. One method to generate this phase shift is to use the PLL to generate a local oscillator that is a multiple of the optical oscillation frequency, for instance 16 times the frequency, using a counter or flip-flop in the feedback loop. This higher frequency clock can be used to clock a shift register to generate the phase shift needed to get positive feedback around the loop, or equivalent digital circuits can be used. A further benefit of this approach is that the electronic shift can be changed in well-defined values, to get a desired phase shift by the cavity. If the feedback condition requires a −45° phase shift, then $\tan(-45°)=-1$, so $f=1/(2\pi\tau)$. If the electronic phase is changed so that the feedback condition requires a cavity phase shift of −22.5°, then the oscillation frequency will change to $f=0.41/(2\pi\tau)$. This may be useful to extend the dynamic range to cover a wide range of cavity lifetimes T without the need to handle a wide range of frequencies. This method may also be useful to check for or correct for non-exponential decay signals, similar to the approach of Loock.

Electronics for reading out the frequency or period of the oscillation include counters or frequency to voltage converters or similar circuits, followed by circuits that can display or digitize the voltage, in addition to the digital frequency synthesis method described above. In the case of the phase-locked loop, it is also possible to measure the voltage of the voltage-controlled oscillator used to generate the locked oscillator. In some cases it may be possible to connect the oscillation frequency to audio speakers and listen for the change in pitch associated with increased cavity losses.

In the preferred embodiment, and as readily understood by one of ordinary skill in the art, the apparatus according to the invention will include a general or specific purpose computer or distributed system programmed with computer software implementing the steps described above, which computer software may be in any appropriate computer language, including C++, FORTRAN, BASIC, Java, assembly language, microcode, distributed programming languages, etc. The apparatus may also include a plurality of such computers/distributed systems (e.g., connected over the Internet and/or one or more intranets) in a variety of hardware implementations. For example, data processing can be performed by an appropriately programmed microprocessor, computing cloud, Application Specific Integrated Circuit (ASIC), Field Programmable Gate Array (FPGA), or the like, in conjunction with appropriate memory, network, and bus elements.

Note that in the specification and claims, "about" or "approximately" means within twenty percent (20%) of the numerical amount cited. All computer software disclosed herein may be embodied on any non-transitory computer-readable medium (including combinations of mediums), including without limitation CD-ROMs, DVD-ROMs, hard drives (local or network storage device), USB keys, other removable drives, ROM, and firmware.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A spectrometer comprising:
    an optical cavity;
    a light source capable of producing light at one or more wavelengths transmitted by said cavity and with the light directed at said cavity;
    a detector and optics positioned to collect light transmitted by said cavity;
    feedback electronics causing oscillation of amplitude of the optical signal on said detector at a frequency that is less than the free spectral range of the cavity and that depends on cavity losses; and a sensor measuring the oscillation frequency to determine the cavity losses.

2. The spectrometer of claim 1 wherein said light source is an LED.

3. The spectrometer of claim 1 wherein said light source is a SLED.

4. The spectrometer of claim 1 wherein said light source is a laser.

5. The spectrometer of claim 1 wherein said light source is a lamp.

6. The spectrometer of claim 1 wherein amplitude of said light source is modulated.

7. The spectrometer of claim 1 wherein wavelength or frequency of said light source is modulated so as to modulate the light transmitted by the cavity.

8. The spectrometer of claim 1 wherein said cavity comprises at least two mirrors enclosing a gaseous sample.

9. The spectrometer of claim 1 wherein said cavity comprises at least two mirrors enclosing a liquid sample.

10. The spectrometer of claim 1 wherein said cavity comprises at least two mirrors enclosing a suspension.

11. The spectrometer of claim 1 wherein said cavity comprises one or more surfaces that use total internal reflection arranged so that an evanescent field is in contact with a sample.

12. The spectrometer of claim 1 wherein said cavity comprises an optical fiber made so that an evanescent field of said optical fiber can interact with a sample.

13. The spectrometer of claim 1 wherein said cavity comprises an integrating sphere.

14. The spectrometer of claim 1 additionally comprising one or more amplifiers and/or phase shifters arranged to create self-oscillation at a target frequency.

15. The spectrometer of claim 1 additionally comprising a phase locked loop.

16. The spectrometer of claim 15 wherein said phase locked loop generates a clock signal that is an integer ratio of the oscillation frequency.

17. The spectrometer of claim 16 wherein said clock signal is used to generate a phase-shifted modulation frequency.

18. The spectrometer of claim 17 wherein said clock signal produces a number of preset phases.

19. The spectrometer of claim 18 wherein said preset phases are chosen to keep the oscillation frequency within a target range of frequencies.

20. The spectrometer of claim 18 wherein the oscillation frequency is measured at a number of preset modulation phases and the resulting frequencies are combined to determine an estimate of cavity loss that is substantially independent of multiexponential behavior of the cavity.

* * * * *